United States Patent [19]

Ferrara

[11] 4,326,959
[45] Apr. 27, 1982

[54] BLOOD SEPARATOR AND DISPENSER

[76] Inventor: Louis T. Ferrara, 2988 Ave. T, Brooklyn, N.Y. 11229

[21] Appl. No.: 231,490

[22] Filed: Feb. 4, 1981

[51] Int. Cl.³ .............................................. B01D 21/26
[52] U.S. Cl. ................................... 210/515; 210/516; 210/927; 128/218 P; 422/44
[58] Field of Search ............... 210/516, 927, 341, 340, 210/399, 515, 800, 801, 540, 539; 128/218 P; 422/44, 72

[56] References Cited

U.S. PATENT DOCUMENTS

| | | | |
|---|---|---|---|
| 3,355,098 | 11/1967 | Farr | 210/540 |
| 3,512,940 | 5/1970 | Shapiro | 210/927 |
| 3,837,376 | 9/1974 | Brown et al. | 210/540 |
| 4,057,499 | 11/1977 | Buono | 210/927 |

*Primary Examiner*—Benoit Castel

[57] ABSTRACT

A serum and cell separating and dispensing device comprising an elongated tubular vessel partitioned throughout its length forming two distinct compartments containing vent orifices on either side. One open end of the vessel is fitted with a resilient element containing a larger and smaller orifice respectively. These orifices communicate with the two compartments respectively. At the opposite end of the vessel are two small tubular vessels extending from and communicating with the compartments formed by the partition. Blood drawn in an evacuated collection tube such as Becton Dickinson's vacutainer is centrifuged after clotting. The device is forced into the open end of the collection tube and pressed downwardly. The resilient element forms an air trap by touching the inner wall of the collection tube and serum is forced through the orifice communicating with the serum compartment. The tubular vessel is turned slightly while the resilient element remains stationary and by so doing, the orifice communicating with the cellular compartment is open while the orifice of the serum compartment is closed. One may then tilt the entire assembly in one direction allowing drops of serum to be dispensed, whereas turning or tiping in the opposite direction allows one to dispense cells in a dropwise manner.

4 Claims, 3 Drawing Figures

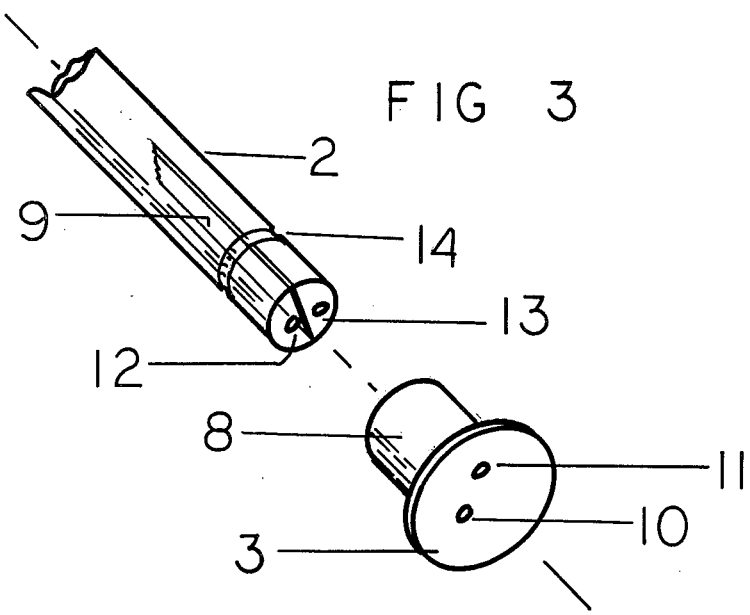
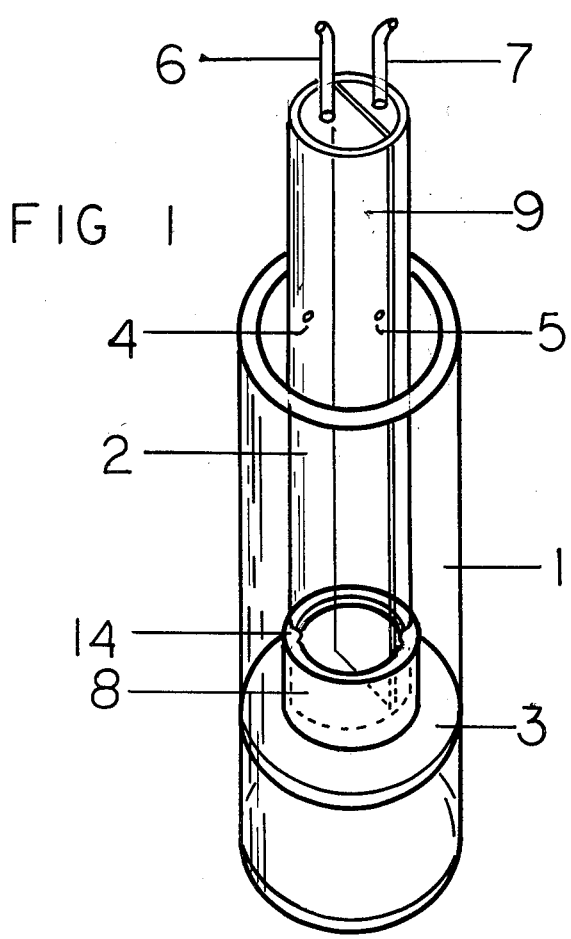
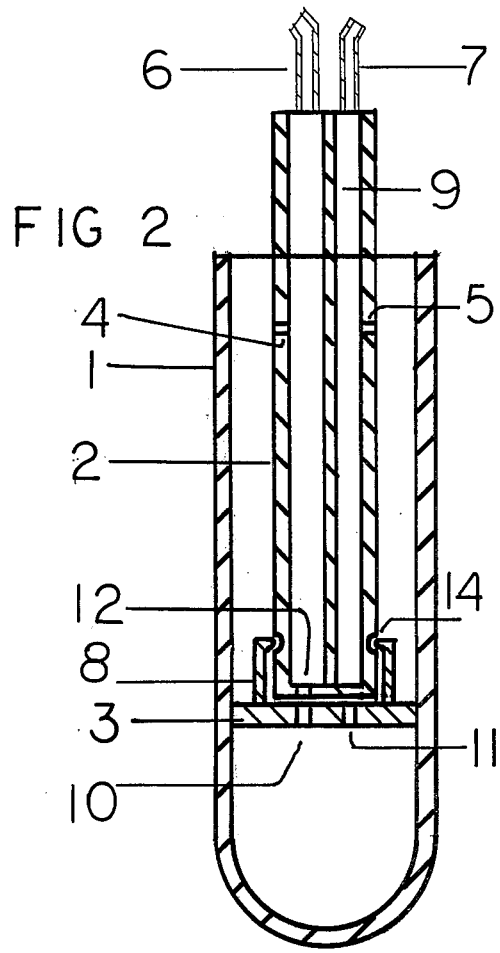

BLOOD SEPARATOR AND DISPENSER

BACKGROUND OF INVENTION

The above abstract relates to a patent applied for by this inventor in 1978, Ser. No. 915,530. This and another application reflects a further modification of said invention.

The invention relates to the dispensing in a dropwise manner of serum and cells in the area of blood banking where blood may be typed and crossmatched for a prospective recipient. It is the custom to obtain a sample of blood by using an evacuated blood collection tube in conjunction with a special cannula. After blood is obtained by vena puncture it is allowed to clot within the confines of the collection tube whereby it is subsequently centrifuged for the purpose of separating the serum and cells. After centrifuging, serum is aspirated or poured into a similar container or tube and labeled. During the process of typing and crossmatching this recipient's blood, serum and cells are required in various amounts of approximately one to three drops for each determination. For example, a front typing may require three drops of cells to be dispensed, ie, one drop for each anti serum on a slide or tube respectively.

In a similar manner serum must also be dispensed for the backtyping procedure and for the crossmatching as well. This is presently being done with a dropper type dispenser pipet. Blood or serum is drawn by the suction of a bulb into the pipet whereby it is subsequently dispensed as described. The use of these squeeze bulb pipets or medicine dropper type dispensers becomes somewhat tedious especially when many typings and crossmatchings must be done. There is also the fact that one may have to use the same specimen again and thus require a fresh dispensing pipet.

SUMMARY AND OBJECTIVES OF INVENTION

It is the object of this invention to provide a means to expedite the separation and dispensing of serum and cells for crossmatching procedures and similar purposes while at the same time maintaining the integrity of the patient's specimen. It is also the object of the invention to provide a device which can separate or segregate serum and cells simultaneously in one vessel which is partitioned in such a manner that serum and cells are directed into these compartments via orifices at the serum or cellular sites; these orifices communicating with said compartments. It is also the object to provide a means of easily dispensing in a dropwise manner each of the blood components namely serum and cells by merely tilting the device or assembly to one side so that drops are dispensed of one component while the other component remains intact in the adjacent compartment. In a similar manner the assembly may be rotated and subsequently tilted to dispense the other component. These components being cells and serum respectively. It is also the object to provide in such a device a means to vent both compartments so as to facilitate the dispensing of each component. It is also the object of the invention to combine compartment size, appropriate venting and dispensing orifice means so that uniform drops of serum or cells are dispensed in such a manner that drops may be counted so that the cells or serum does not run out or "leak" in a haphazard manner. A further objective of the invention would be to eliminate both the pipets and tubes presently being used. The latter must be labelled with the patient's complete identification such as hospital number, complete name etc. This would be eliminated due to the fact that the original blood collection tube is required to have all items of identification and the separation of components and dispensing of said components is done with this tube alone. That is to say that the serum need not be transfered to another tube.

DESCRIPTION OF DRAWINGS

FIG. 1 shows blood collection tube 1 with the dispensing device 2 within its confines.

FIG. 2 is an elongated cross sectional view of the collection tube 1 having within its confines the device 2

FIG. 3 shows a diagonal view of the device in an exploded fashion.

DETAILS OF DRAWING

In FIG. 1 the separator-dispensing device comprises; a tubular element or vessel 2 separated or partitioned by a wall 9 which runs vertically relative to vessel 2. The lower end of the tubular vessel 2 is fitted with a resilient element 8. At the top of vessel 2 are two dispensing spouts 6 and 7 which are curved to either side of said vessel. Said spouts containing orifices which are directed in opposition to each other such that when one orifice is in a tilt position to dispense, the other is in an upward or non-dispensing position. FIG. 1 also shows vent holes 4 and 5 respectively being oriented on either side of the element 9 which forms both compartments.

FIG. 2 shows an elongated cross sectional view of the device 2 within a blood collection tube 1. The entire assembly may be made of plastic material or combination of plastic and rubber. That is to say that the resilient element 8 would be rubber or one of the synthetic rubbers or resilient material, while the remaining portion of the device 2 is constructed of plastic. It is possible, and probably in the preferred embodiment that the entire device be constructed of plastic. The essential features however must coincide with the objectives of the invention.

Referring to FIG. 2 the elongated portion of element 2 is shown fitted into resilient element 8 which contains or is permanently affixed to flange 3, also shown in FIG. 1 and FIG. 3. Said vessel 2 has at its bottom end or resilient element end a notch that runs around it or circumvents it. Refer to FIG. 3, element 14. FIG. 2 shows how the notched portion of element 2 receives resilient element 8. The idea behind this is so that element 2 may be turned or rotated slightly while resilient element 8 remains stationary, it being held by friction against the wall of the blood collection tube 1 by flange 3. FIG. 2 also shows orifices 10, 11, and 12 respectively. Two of these orifices, 10 and 11 penetrate flange 3 and communicate with orifices 12 and 13 located on the underside of element 2. FIG. 2 only shows orifices 10, 11, and 12. FIG. 3 shows all four. In other words FIG. 2 shows orifices 10 and 12 in communication with each other and in communication with the compartment bearing said orifice 12. Orifice 13 is closed off relative to orifice 11. The reason for this will become apparent in the operation of the device.

Referring to FIG. 3, this shows an exploded diagonal view of the invention. Orifices 12 and 13 respectively are shown on the underside of the tubular portion of element 2., while orifices 10, & 11 are shown on the underside of flange 3. The respective orifices 10, 11, 12, & 13 are so oriented on their respective parts, that is, tubular element 2 and resilient element 8 that communication with the two compartments cannot be simultaneously made. That is to say that if communication to one compartment is made via orifice 10 and 12 then orifice 11 and 13 are closed off to each other and thus the compartment relative to these is closed off. In the same respect when 11 and 13 are opened to each other 10 and 12 are closed off.

OPERATION OF INVENTION

Blood is drawn by vena puncture in a tube such as Becton Dickinson's vacutainer tube. The blood in this tube is allowed to clot and the tube centrifuged. This procedure seperates the blood into a upper serum portion and a lower portion containing clot and loose red cells. The device herein described in FIG. 1 and FIG. 2 is then placed into the upper portion of the tube 1 with flange 3 entering first. Flange 3 is made wider than the opening or mouth of the collection tube 1 and begins to distort itself as it presses against the walls of tube 1. As tubular element 2 is pressed down resilient element or flange 3 begins to contact the serum portion which is on top. The resistance of the flange 3 against the walls of the tube plus the compression of air in consequence of this establishes a resistance relative to the serum which is being compressed. Orifices 10 and 12 being opened to each other, FIG. 2 and mediating the compartment generating orifice 12 allows the serum to enter that compartment due to there being less resistance at that point. Tubular element 2 is then turned slightly either clockwise or counter clockwise thus closing off communication with orifices 10 and 12 and thereby opening communication with orifices 11 and 13 and their respective compartment. The compartment containing the serum remains closed while the compartment which will contain the cells remains opened. In other words, due to the relative locations of the serum with respect to the clot and loose cells it is necessary to collect or compartamentalize the serum which is on top first. Therefore the two respective orifices 10 and 12 must be initially in the opened position and would be placed that way in manufacture. One can then grasp the device and immediately press down into the serum collecting this portion first. The tubular element 2 would then simply be twisted slightly in either direction while the resilient element 8 is held relatively secured by flange 3 against the walls of tube 1. Cells would then be available from the bottom of said tube 1 and can communicate easily to the cellular compartment via the respective orifices of said compartment 11 and 13. Note that it is not necessary or even desirable to continue to press the device, tubular element 2 downwardly as was done in order to compartmentalize the serum. In fact further downward pressure may cause cells to leak through into the serum compartment even if closed off. This may however be overcome by seating element 2 into resilient element 8 in a more tighter manner. This must however take into consideration that said tubular element 2 must be able to rotate slightly within the confines of resilient element 8 which operates together to open and close the aforementioned orifices. Once the serum compartment is substantially filled and closed off the entire assembly tube 1 containing device 2 may be tilted to dispense serum. Tilting the assembly in the opposite direction allows cells to flow from the bottom of tube 1 through orifices 11 and 13 and subsequently into the cellular compartment and out of the respective spout in a dropwise manner.

With respect to the rotation of tubular element 2 which operates to open and close orifices communicating respectively with the serum and cellular compartment it should be noted that after serum is confined to its compartment, rotation of element 2 may be governed by some marking on this element relative to a marking on resilient element 8. Such markings would indicate alignment or non alignment of the serum compartment orifices and those of the cellular compartment. In other words the manufacture would align tubular element 2 so that the serum compartment is in the opened position. After serum is collected in its compartment one would twist the tubular element slightly in such a manner so as to align the markers. This would then indicate the opening of the orifices communicating with the cellular compartment.

In order for serum or cells to be dispensed a vent system must exist. This is shown FIG. 1 and FIG. 2 as elements 4 and 5. In this respect the size of the vents relative to the amount of serum passing through plus considerations relating to the spouts such as size of spouts' orifice and bend all must be considered. Serum clogging these orifices or vents 4 and 5 would hinder dispensing. If the size of the compartment is made larger relative to the amount of maximum serum that would be collected then the serum would pass under the orifices or vents and not clog them.

Having fully described my invention I claim:

1. A blood separating device adapted for use with a blood centrifuge tube, said blood separating device comprising:

an elongated rotatable tubular member having a first open end and second end, said second end being closed except for two radially spaced openings, said tubular member having an outer diameter less than the inner diameter of said blood centrifuge tube; partitioning means to longitudinally partition said tubular member into a first compartment and a second compartment, one of said radially spaced opening in said second end communicating with said first compartment, and the other radially spaced opening in said second end communicating with said second compartment;

First vent means located on the circumferential wall of the tubular member and communicating with said first compartment, for venting air therefrom;

second vent means located on the circumferential wall and diametrically opposed from said first vent means, and communicating with said second compartment, for venting air therefrom, first dispensing means communicating with said first compartment at the first end of said tubular member, for dispensing drops from said first compartment;

second dispensing means communicating with said second compartment at the first end of said tubular member, for dispensing drops from said second compartment, said first and second dispensing means being constructed and arranged to enable dispensing from only one of said first or second compartment at a time;

resilient element means fitted in sealing relationship with the second end of said tubular member, and having a first orifice capable of being brought into communication with said one radially spaced opening in said second end, and a second orifice capable of being brought into communication with said other radially spaced opening in said second end, said resilient element means comprising flange means constructed and arranged to sealingly engage with the inner wall of said blood centrifuge tube, said tubular member further comprising a circumferential groove, said resilient means further comprising a notch cooperating with said circumferential groove such that rotation of said tubular member only enables communications of either said one radially spaced opening with said first orifice or said other radially spaced opening with said second orifice.

2. A blood separating device as recited in claim 1, wherein said tubular member has markings affixed thereon.

3. A blood separating device as recited in claim 1, wherein said resilient element means has markings affixed thereon.

4. A blood separating device as recited in claim 2, wherein alignment of the markings on the tubular member with those on the resilient element means is indicative of fluid communication between said one radially spaced opening and said first orifice.

* * * * *